(12) United States Patent
Bunner et al.

(10) Patent No.: US 9,169,934 B2
(45) Date of Patent: Oct. 27, 2015

(54) HIGH PRESSURE FLUIDIC SWITCHING VALVE HAVING VARIABLE PRESSURE LOADING

(75) Inventors: Bernard Bunner, Newton, MA (US); Joseph Michienzi, Plainville, MA (US); Keith Fadgen, Hope Valley, RI (US)

(73) Assignee: Waters Technologies Corporation, Milford, MA (US)

( * ) Notice: Subject to any disclaimer, the term of this patent is extended or adjusted under 35 U.S.C. 154(b) by 57 days.

(21) Appl. No.: 14/114,330

(22) PCT Filed: Apr. 24, 2012

(86) PCT No.: PCT/US2012/034760
§ 371 (c)(1),
(2), (4) Date: Oct. 28, 2013

(87) PCT Pub. No.: WO2012/151080
PCT Pub. Date: Nov. 8, 2012

(65) Prior Publication Data
US 2014/0053910 A1    Feb. 27, 2014

Related U.S. Application Data

(60) Provisional application No. 61/482,647, filed on May 5, 2011.

(51) Int. Cl.
*F16K 3/10* (2006.01)
*F16K 3/18* (2006.01)
(Continued)

(52) U.S. Cl.
CPC ... *F16K 3/10* (2013.01); *F16K 3/18* (2013.01); *F16K 31/041* (2013.01); *G01N 35/1097* (2013.01); *G01N 2030/202* (2013.01); *Y10T 137/0318* (2015.04)

(58) Field of Classification Search
CPC ........... F16K 3/10; F16K 3/18; F16K 31/041; G01N 35/1097; G01N 2030/202; Y10T 137/0318
USPC ..................... 251/180, 129.06, 129.11; 137/1
See application file for complete search history.

(56) References Cited

U.S. PATENT DOCUMENTS 4,476,731 A * 10/1984 Charney et al. ............... 251/149
4,577,515 A *  3/1986 Someya et al. ............ 73/863.73
(Continued)

FOREIGN PATENT DOCUMENTS

| CN | 1700018 A | 11/2005 |
|---|---|---|
| GB | 1438275 | 6/1976 |
| JP | 2001032950 | 2/2001 |

OTHER PUBLICATIONS

International Preliminary Report on Patentability in counterpart international patent application No. PCT/US12/34760, mailed on Nov. 14, 2013; 7 pages.

(Continued)

*Primary Examiner* — John Bastianelli
(74) *Attorney, Agent, or Firm* — Schmeiser, Olsen & Watts LLP; William G. Guerin

(57) ABSTRACT

A method for switching a high pressure fluid includes applying a fixed force between a planar surface of a rotor and a planar surface of a stator. The planar surface of the rotor includes a fluidic channel and the planar surface of the stator has a pair of ports to receive and provide the fluid. A control signal is applied to a linear actuator coupled to the rotor to generate a controllable force between the planar surfaces of the rotor and stator. The control signal is responsive to a rotational state of the rotor. The total force between the planar surfaces of the rotor and the stator is substantially equal to a sum of the fixed force and the controllable force. The method reduces the wear and extends the lifetime of components in a rotary shear seal valve.

12 Claims, 5 Drawing Sheets

(51) Int. Cl.
*F16K 31/04* (2006.01)
*G01N 35/10* (2006.01)
*G01N 30/20* (2006.01)

(56) References Cited

U.S. PATENT DOCUMENTS

| | | | |
|---|---|---|---|
| 4,890,645 A | 1/1990 | Andersen | |
| 6,193,213 B1 | 2/2001 | Stearns et al. | |
| 6,267,143 B1* | 7/2001 | Schick | 137/625.11 |
| 7,308,908 B2* | 12/2007 | Keene et al. | 137/625.46 |
| 2008/0135792 A1 | 6/2008 | Armiroli et al. | |
| 2008/0308079 A1 | 12/2008 | Albert | |
| 2009/0320925 A1 | 12/2009 | Nichols | |
| 2010/0281959 A1* | 11/2010 | Berndt | 251/368 |
| 2011/0006237 A1 | 1/2011 | Tower | |

OTHER PUBLICATIONS

First Office Action in related Chinese Patent Application No. 201280021869.3, issued on Dec. 3, 2014; 28 pages.

International Search Report and Written Opinion in related international patent application No. PCT/US12/34760, mailed on Jul. 31, 2012; 8 pages.

Extended European Search Report in counterpart European patent application No. 12779916, mailed on Oct. 6, 2014; 7 pages.

* cited by examiner

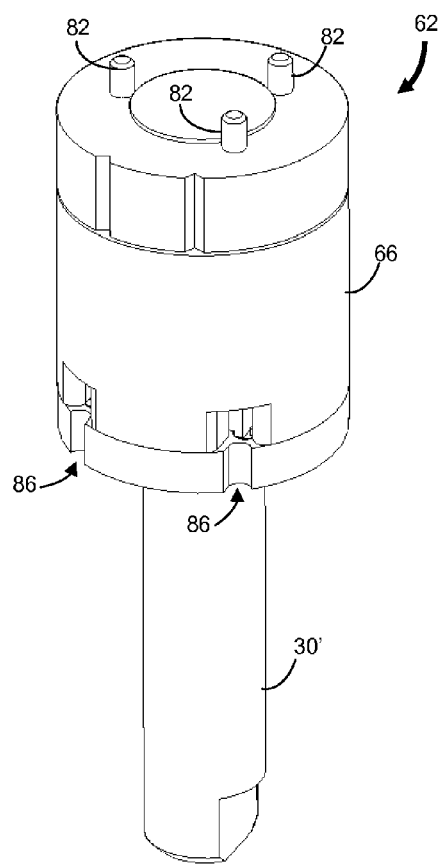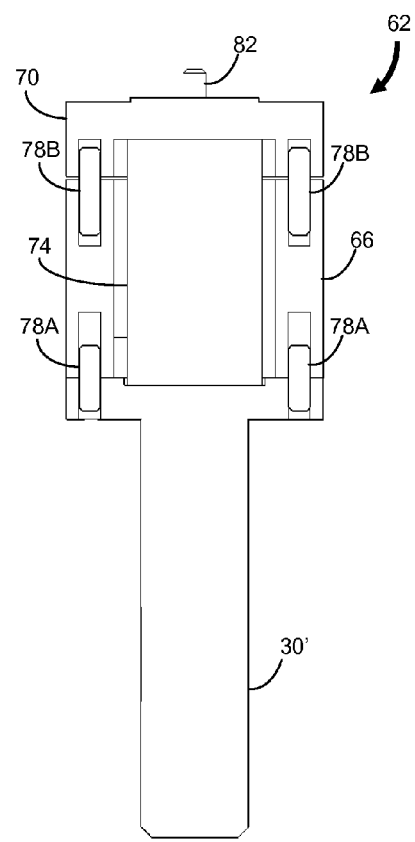
*FIG. 2A*  *FIG. 2B*

HIGH PRESSURE FLUIDIC SWITCHING VALVE HAVING VARIABLE PRESSURE LOADING

RELATED APPLICATION

This application claims the benefit of the earlier filing date of U.S. Provisional Patent Application Ser. No. 61/482,647, filed May 5, 2011 and titled "High Pressure Fluidic Switching Valve Having Variable Pressure Loading," the entirety of which is incorporated herein by reference.

FIELD OF THE INVENTION

The invention relates generally to valves for switching high pressure fluids. More particularly, the invention relates to a rotary shear seal valve having applications in liquid chromatography systems.

BACKGROUND

Liquid chromatography measurement systems such as high performance liquid chromatography (HPLC) and ultra HPLC (UPLC®) systems typically employ injection valves having a rotary shear seal. A force of several hundreds of pounds or more is applied between the rotor and stator to seal against pressures that can exceed 15,000 psi. The force is maintained while the rotor rotates between valve switch positions, thereby placing stringent requirements on the quality of the sealing surfaces. The injection valves are typically intended to operate for tens of thousands of cycles without excessive wear and leakage.

HPLC and UPLC instrument manufacturers anticipate that future instruments will require sealing pressures of injection valves to exceed 20,000 psi. Intrinsic limitations in the material properties of the stator and, in particular, the polymeric rotor are not likely to be overcome with incremental improvements in materials and design.

U.S. Pat. No. 6,193,213 discloses a method for varying the force or pressure applied between the stator and the rotor during rotation of the rotor in a conventional rotary shear injection valve. In particular, a lower force is applied when the required sealing pressure is low or when the injection valve is rotated between two switch positions to reduce wear. A greater force is generated at other times to maintain a proper seal and when the valve is not in transition between switch positions. The force applied between the stator and the rotor is controlled by the pressure of a fluid supplied to the injection valve. This technique requires high-pressure fluid control and sealing to operate. One significant disadvantage is the potential for leakage of the hydraulic fluid used to vary the applied force.

The present invention addresses the need for a high pressure rotary seal valve that overcomes the problems identified above and can seal to pressures greater than 20,000 psi for tens of thousands of cycles.

SUMMARY

In one aspect, the invention features a rotary shear seal valve that includes a rotor shaft, linear actuator, rotor and stator. The linear actuator is secured to the rotor shaft and is configured to apply a force directed parallel to a shaft axis of the rotor shaft in response to an applied electrical signal. The force has a magnitude responsive to the applied electrical signal. The rotor has a planar surface with a fluidic channel therein. The rotor is coupled to the linear actuator and configured to rotate about the shaft axis. The stator has a planar surface disposed parallel to and in contact with the planar surface of the rotor. The planar surface of the stator has a first port to receive a fluid and a second port to provide the fluid. The fluidic channel conducts the fluid received at the first port to the second port when the rotor is in a first switch position and the fluid is prevented from flowing from the first port to the second port when the rotor is in a second switch position.

In another aspect, the invention features a method for switching a high pressure fluid. The method includes applying a fixed force between a planar surface of a rotor and a planar surface of a stator. The planar surface of the rotor has a fluidic channel therein and the planar surface of the stator has a first port to receive a fluid and a second port to provide the fluid. The method further includes applying a control signal to a linear actuator coupled to the rotor to thereby generate a controllable force between the planar surface of the rotor and the planar surface of the stator. The control signal is responsive to a rotational state of the rotor. A total force between the planar surfaces of the rotor and the stator is substantially equal to a sum of the fixed force and the controllable force.

In still another aspect, the invention features a method for switching a high pressure fluid. According to the method a combination of a first force and a second force is applied to an interface of a surface of a rotor and a surface of a stator. The first force is substantially constant and the second force has a magnitude that is responsive to an electrical control signal. The planar surface of the rotor has a fluidic channel therein and the planar surface of the stator has a first port to receive a fluid and a second port to provide the fluid. A state of the electrical control signal is changed to reduce the magnitude of the second force. The rotor is rotated from a first switch position to a second switch position while the magnitude of the second force is reduced. The state of the electrical control signal is changed to increase the magnitude of the second force when the rotor is at the second switch position.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

FIGS. 2A and 2B show views of an embodiment of a subassembly for a rotary shear seal valve according to the invention.

DETAILED DESCRIPTION

Figure 1A:
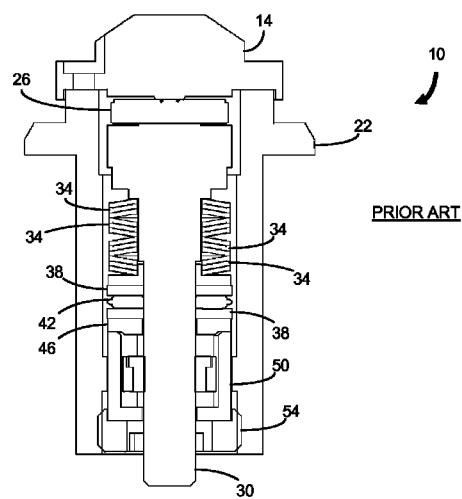
FIGS. 1A and 1B are a cross-sectional view and a top view, respectively, of an HPLC 6-port injection valve.

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

In brief overview, the invention relates to a rotary shear seal valve capable of operating for an extended lifetime at high pressures such as those encountered when used as an injection valve in HPLC and UPLC systems. It will be recognized that the method and apparatus described herein can be adapted for switching of high pressure fluidic paths in other applications. The rotary shear seal valve includes a linear actuator configured to apply a variable force to an interface of sealing surfaces. The linear actuator can be an electrical actuator such as a piezoelectric actuator. Alternatively, the linear actuator can be a mechanical actuator such as a piston drive or cam drive actuator. Still other examples of actuators that can be used include hydraulic and pneumatic actuators. Thus the variable force can be an electromotive force, an electromagnetic force and/or other suitable type of force.

The valve can be fabricated using materials similar to those in conventional injection valves. For example, either the rotor or the stator is fabricated from a strong polymeric material, such as polyether ether ketone (PEEK) or carbon-reinforced PEEK, and the other component is fabricated from a metal that is coated with a diamond-like coating (DLC). The polymer and the DLC coating yield a low coefficient of friction and result in reduced wear and leakage over time.

The rotary shear seal valve is assembled so that a fixed force, referred to as a preload force, is applied between the rotor and stator. In various embodiments described below the linear actuator is a piezoelectric actuator. Advantageously, the piezoelectric actuator can be used as a sensor during assembly to measure the preload force and to set the preload force to the desired value. After assembly, the piezoelectric actuator is used to create an additional, variable force between the rotor and stator. The magnitude of the variable force is determined by an electrical signal supplied to the piezoelectric actuator by a high-voltage, low-current power supply. When the sealing pressure for the valve is intended to be small, such as when the rotor rotates between the valve angular states, the variable force applied by the piezoelectric actuator is set to zero or to a small value so that the total force on the sealing surfaces is substantially equal to the preload force. Although this may allow leakage between the sealing surfaces, valve rotation is typically rapid; occurring in milliseconds or tens off milliseconds, thus the amount of leakage is small. When the rotor is stationary, i.e., when the rotary shear valve is not changing states, the variable force applied by the piezoelectric actuator is greater than the preload force. The total force is the sum of the preload force and variable force, and is set to be sufficiently large to achieve the required seal to the desired pressure. Advantageously, the lower force during valve rotation results in lower wear and consequently extended life of the rotor and stator.

Figure 1B:
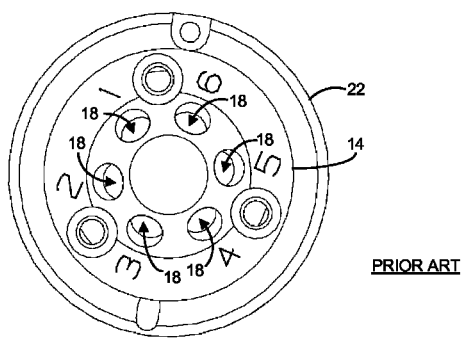

FIG. 1A and FIG. 1B show a cross-sectional view and a top view, respectively, of an HPLC 6-port injection valve 10 based on a rotary shear seal.

A stator 14 is secured to a valve housing 22 and has six ports 18 and a substantially planar stator face (not visible). Each port 18 is configured for coupling to a fluidic tube (or channel) that supplies fluid to the valve 10 or receives fluid from the valve 10. The housing 22 substantially encloses a rotor 26, rotor shaft 30, Belleville spring washers (shown as four stacks having three washers 34 per stack), bearing washers 38, thrust bearing 42, loading washer 46, loading spider 50 and loading nut 54.

The rotor 26 is secured to the rotor shaft 30 and has a substantially planar rotor face that is parallel to and in contact with the stator face. An axial force is applied to the rotor 26 by the Belleville spring washers 34 which are locked in place by the loading nut 54. The axial force is used to urge the rotor face against the stator face and thereby maintain a fluidic seal at the interface of the rotor and stator faces. The magnitude of the axial force can be adjusted by turning the loading nut 54.

Grooves in the rotor face are configured to couple various ports 18 of the stator 14 with other ports 18 when the rotor 26 and stator 14 are in certain rotational alignments. In UPLC instruments, the pressure of the fluid circulating through the ports can exceed 15,000 psi and may be as great as 20,000 psi or more. The Belleville spring washers 34 provide a force to form the fluidic seal between the stator and rotor faces. The rate of leakage is typically hundreds of nanoliters per minute. The force applied by the spring washers 34 can be a few hundred pounds and may be as great as 500 lbs. or more.

Rotation of the rotor 26 with respect to the stator 14 changes the connectivity of the ports 18. Rotation is facilitated by the thrust bearing 42. The force applied by the Belleville spring washers 34 is maintained during rotation. As a result, high shear forces are applied to the sealing surfaces. In various embodiments, the rotor face is formed in a PEEK or carbon-reinforced PEEK material and the stator face is formed in a metallic material coated with a thin layer of DLC that dramatically reduces the friction between the stator and rotor face. These combinations of materials have been demonstrated to achieve excellent sealing for tens of thousands of cycles of valve rotation.

The trend to greater operating pressures may be beyond the capabilities of the conventional design and materials of the injection valve 10. It is possible to increase the force applied by the Belleville spring washers 34; however, the increased force typically results in faster wear of the rotor face and stator face, with an associated increased leakage and reduced valve lifetime.

Wear is primarily caused by the high shear force applied during rotation of the rotor 26 when changing the rotational state of the injection valve 10. The high shear force is due to the high axial force applied between the stator 14 and the rotor 26 to create the high-pressure fluidic seal.

FIG. 2A illustrates a subassembly 62 for a rotary shear seal valve according to the invention. The subassembly 62 includes a rotor shaft 30', an actuator housing 66 and an actuator cap 70. FIG. 2B illustrates a cross-sectional view of the subassembly 62 where a piezoelectric actuator 74 and pins 78A and 78B are visible.

Three pins 82 extending from the actuator cap 70 serve to locate and fix the rotor 26 to the cap 70. Other pins 78 disposed in the rotor shaft 30', actuator housing 60 and actuator cap 70 ensure that the subassembly 62 rotates as a single unit and prevent damage that otherwise would occur due to torsion of the piezoelectric actuator 74. The lower pins 78A and their corresponding holes are dimensioned to form interference fits so that there is no relative rotational motion between the actuator housing 66 and the rotor shaft 30'. The upper pins 78B and their corresponding holes are dimensioned to form sliding fits so that the actuator cap 70 can translate freely but not rotate relative to the actuator housing 66.

In some embodiments, the piezoelectric actuator 74 includes a piezoelectric stack that has a number of layers of piezoelectric ceramic material. Piezoelectric stacks suitable for various embodiments are commercially-available and have layers of piezoelectric material that are typically less than 100 μm thick. Each layer is separated from an adjacent layer by a thin electrically-conductive metallic layer. The metallic layers are connected in alternating fashion to a positive conductor or a negative conductor. Application of a voltage between the positive and negative conductors results in elongation of each layer and consequently elongation of the piezoelectric stack. In one embodiment, the piezoelectric stack is a 10 mm×10 mm by 18 mm commercially available device (P-888.50 from Physik Instrumente (PI) L.P.) having a maximum operating voltage of 120 V corresponding to a maximum elongation of 18 μm. At maximum elongation, the blocking force is 800 lbs. force or, equivalently, a compressive force of 800 lbs. is required to prevent elongation at the maximum operating voltage.

The piezoelectric actuator 74 is controlled by a voltage applied between two conductors that exit the piezoelectric housing 66 through two openings 86. When the piezoelectric actuator 74 is energized by the applied voltage, elongation of the piezoelectric stack causes the actuator cap 70 to push the rotor 26 toward the stator 14. When the voltage is reduced or eliminated, the reduction in force applied by the piezoelectric actuator 74 during rotation of the rotor results in a reduction of the shear force between the stator and rotor faces. Consequently, the wear of the stator and rotor faces is substantially reduced, resulting in a longer operating live for the injection valve 10.

Figure 3:
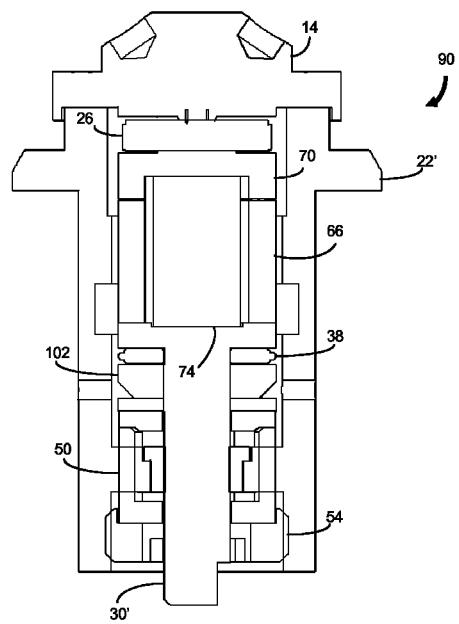
FIG. 3 is an illustration of an embodiment of a rotary shear seal valve that includes the subassembly of FIGS. 2A and 2B.

FIG. 3 shows an embodiment of a rotary shear seal valve 90 according to the invention. The valve 90 includes the subassembly 62 of FIGS. 2A and 2B enclosed within a valve housing 22'. There are no spring washers in the illustrated embodiment. The valve 90 is preloaded by turning the loading nut 54 and using the piezoelectric actuator 74 as a sensor to measure the resulting force. When the desired preload force is achieved, the piezoelectric stack actuator 74 is electrically coupled to a power supply. In one embodiment, the power supply generates a voltage in a range of 0 V to 120 V. The maximum fluid pressure $P_{max}$ at which the stator and rotor faces remain sealed can be determined experimentally.

Piezoelectric stack actuators are limited by their small maximum displacement or elongation. As a result, the mechanical structure that holds the piezoelectric actuator 74 is preferably as stiff as possible. Insufficient stiffness of the various components, including the loading spider 50, washers, thrust bearing 38, rotor shaft 30', housing 22' and actuator cap 70, can limit the force that pushes the rotor 26 against the stator 14.

The maximum sealing force of the rotary shear seal valve 90 is dependent on the geometry of the piezoelectric actuator 74 and the maximum voltage that can be applied. For example, the length of the piezoelectric actuator can be increased along with the length of the housing 22' to obtain a greater sealing force.

Figure 4:
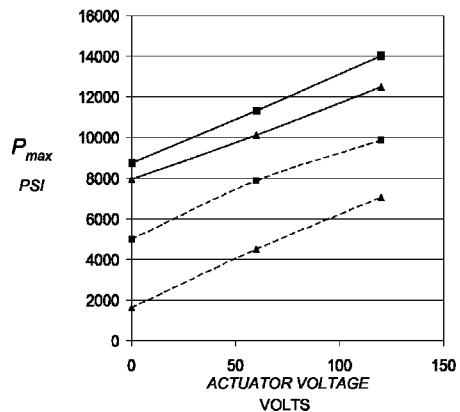
FIG. 4 is a graphical depiction of an example of how a maximum fluid sealing pressure varies as a function of a voltage applied to a piezoelectric actuator for different preload forces.

FIG. 4 graphically illustrates an example showing the maximum fluid sealing pressure $P_{max}$ as a function of the voltage applied to the piezoelectric actuator 74 for different preload forces. The increase in sealing pressure $P_{max}$ is substantially linear with respect to an increase in the voltage applied to the piezoelectric actuator 74. Moreover, the contribution of the preload force and the force applied by the piezoelectric actuator 74 are additive. In the illustrated example, the piezoelectric actuator 74 increases the sealing pressure by approximately 5000 psi for 120 V. For example, in order to achieve a static sealing pressure of 20,000 psi with the actuator 74, the preload force is set to 15,000 psi.

The use of a piezoelectric actuator that responds according to FIG. 4 can enable sealing for fluid pressures that exceed 20,000 psi by combining the controllable force applied by the actuator in combination with typical preload forces achieved with conventional injection valves that operate up to fluid pressures exceeding 15,000 psi.

Figure 5:
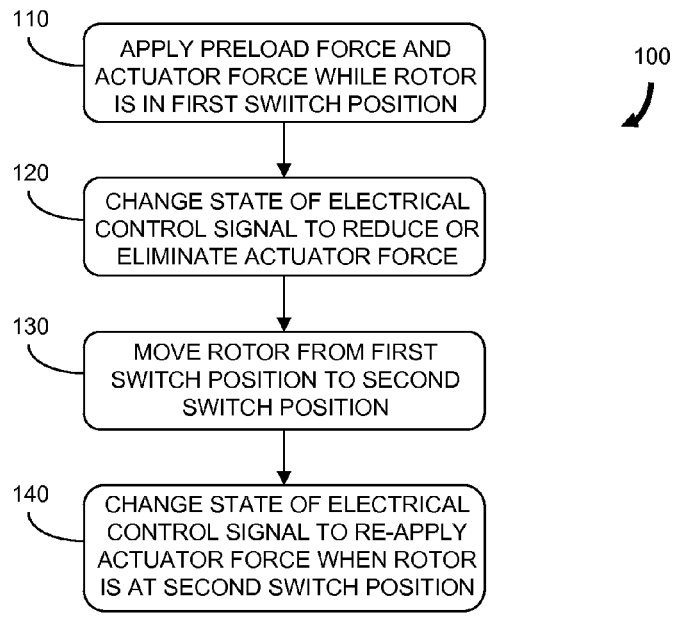
FIG. 5 is a flowchart representation of an embodiment of a method for switching a high pressure fluid according to the invention.
Figure 6:
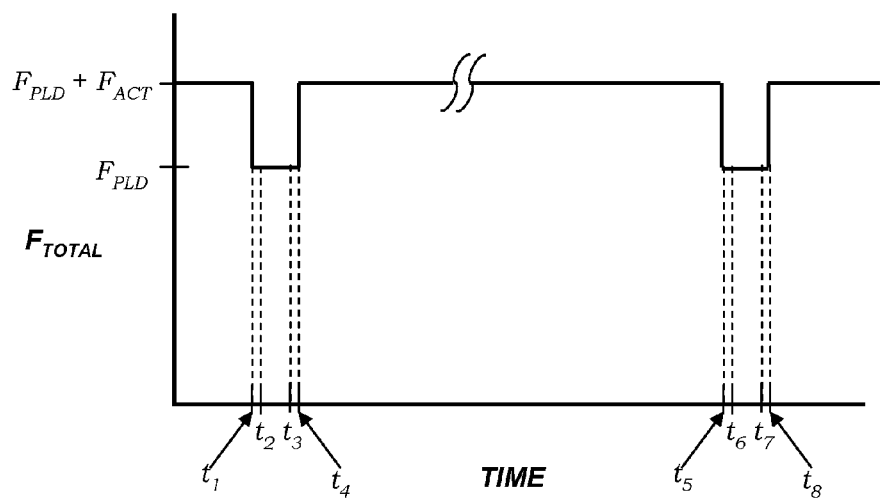
FIG. 6 is a graphical depiction of an example of the force applied to the interface of the planar surfaces of a stator and rotor in time during performance of the method of FIG. 5.

FIG. 5 is a flowchart representation of an embodiment of a method 100 for switching a high pressure fluid that can be practiced using, for example, the rotary shear seal valve 90 of FIG. 3. FIG. 6 graphically depicts the force applied to the interface of the planar surfaces of the stator 14 and rotor 26 in time during performance of the method 100.

According to the method 100, a combination of a first force and a second force urge (step 110) the planar surface of the rotor 26 against the planar surface of the stator 14 while the rotor 26 is in a first switch position. The first force is the preload force $F_{PLD}$ and the second force is the force $F_{ACT}$ applied by the piezoelectric actuator when energized by an electrical control signal.

At time $t_1$, a change (step 120) in the state of the electrical control signal applied to the piezoelectric actuator 74 causes a reduction or elimination of the actuator force $F_{ACT}$. Thus the total force $F_{TOTAL}$ is substantially equal to the preload force $F_{PLD}$. For example, the voltage of the control signal can be reduced to zero to remove the actuator force $F_{ACT}$. At time $t_2$, the rotor 26 is rotated (step 130) from the first switch position to a second switch position while the only force pushing the rotor 26 toward the stator 14 is the preload force $F_{PLD}$. For example, the rotation may be part of a sample loading sequence or an injection sequence for a liquid chromatography measurement process. Thus the wear on the stator and rotor planar surfaces is similar to the wear that occurs on these surfaces in conventional rotary shear seal valves.

FIG. 6 shows a delay between the time $t_1$ when the control signal changes state and the time $t_2$ when the rotor 26 begins to rotate. This accommodates the finite time (e.g., a few milliseconds) for the actuator to reduce or remove the force $F_{ACT}$.

At time $t_3$ the rotor reaches the second switch position and at time $t_4$ the control signal is returned (step 140) to a maximum operating voltage. Thus the piezoelectric actuator 74 re-applies the actuator force $F_{ACT}$ so that the total force $F_{TOTAL}$ pushing the rotor 26 against the stator 14 is the sum of the two forces $F_{PLD}$ and $F_{ACT}$.

The method 100 can be repeated, for example, at times $t_5$ to $t_8$, to achieve a subsequent switching operation.

It should be noted that in some embodiments the response of the piezoelectric actuator 74 to the control signal may be sufficiently rapid so that the initiation and termination of rotation can be simultaneous with the change in state of the control signal. In such embodiments, the difference between time $t_1$ and time $t_2$ is zero and the difference between time $t_3$ and time $t_4$ is zero.

Leakage can occur during valve switching because of the decrease in the total force $F_{TOTAL}$. In general, leakage is negligible when the time for the rotor 26 to move between switch positions is brief and if the reduction and re-application of the actuator force $F_{ACT}$ are rapid (e.g., a few milliseconds). By way of example, the time for a rotor to move between switch positions is typically less than 500 ms in commercially-available models of conventional rotary shear seal valves. The use of similar rotor components in the rotary shear seal valve according to the invention results in similar switching times with insignificant leakage for most applications. The time for the piezoelectric actuator 74 to retract or elongate, i.e., the non-zero time for the total force $F_{TOTAL}$ to transition between the two values shown in FIG. 6, depends on the magnitude of the electrical current level for the actuator control signal. By way of example, various commercially-available piezoelectric actuators operating at a maximum voltage of 120 V can fully retract or elongate in approximately 1 ms in response to a 1.6 A control signal and full retraction or elongation occurs in approximately 10 ms for a 0.16 A control signal. In steady state when the voltage is maintained at 120 V, the actuator 74 requires little or no current (e.g., a few nanoamperes) due to the capacitive nature of the device. In contrast, alternative forms of actuators capable of generating large forces, such as AC or DC motors, use substantially greater currents during steady state operation to maintain an applied force. Advantageously, piezoelectric stack actuators have virtually infinite lifetimes when pre-compressed such as in this application.

Figure 7:
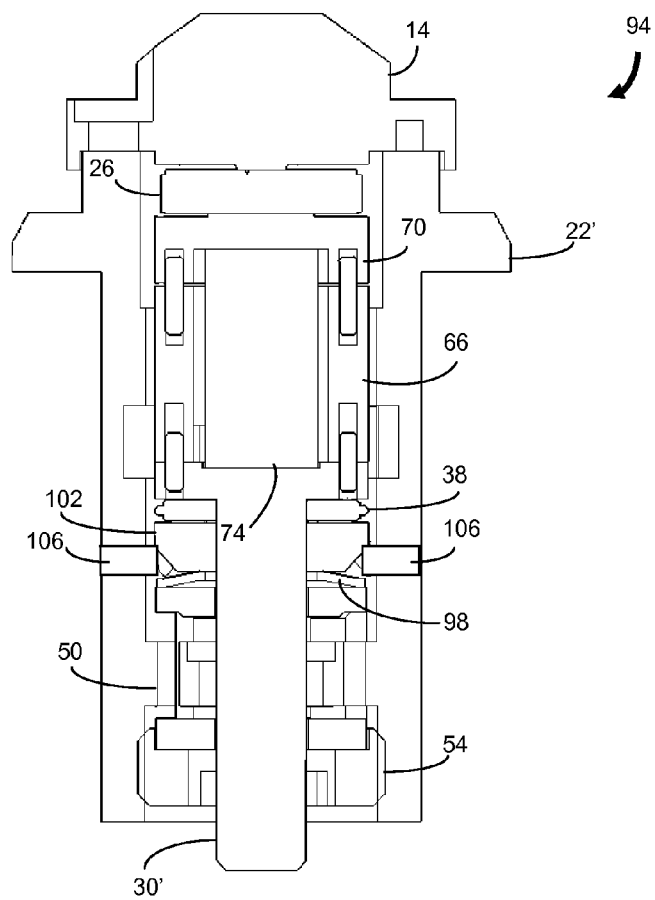
FIG. 7 is an illustration of another embodiment of a rotary shear seal valve according to the invention.

FIG. 7 illustrates another embodiment of a rotary shear seal valve 94 according to the invention. The valve 94 includes similar components to the rotary shear seal valve 90 of FIG. 3; however, a Belleville spring washer 98 is disposed below the support washer 102 in order to provide additional compliance during the preloading of the valve assembly and to improve the ability to set a desired preload. After the desired preload is set, a number of set screws 106 located around the edge of the valve housing 22" are tightened. The set screws 106 contact the bottom angled surface of the support washer 102 to secure it in proper position. In the absence of the set screws 106, the small displacement of the piezoelectric actuator 74 would be absorbed almost entirely by the Belleville spring 98 and, as a result, only a minor additional loading force would be applied to the interface of the stator 14 and the rotor 26.

Figure 8:
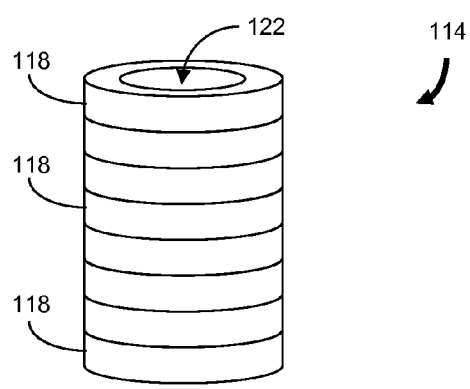
FIG. 8 is an illustration of a piezoelectric stack actuator in the form of a stack of piezoelectric ring elements.

The piezoelectric stack actuators described above can take a variety of forms. In some embodiments, the piezoelectric stack actuator is in the form of a stack 114 of piezoelectric ring elements 118 as shown in FIG. 8. In some of these embodiments, the hollow core 122 accommodates passage of the rotor shaft.

Although embodiments described above generally utilize piezoelectric actuators, a variety of other types of linear actuators can be used. In one example, the linear actuator includes a stepper motor or DC motor that is coupled to one of the rotor or the stator, either directly or through a cam, piston or other mechanical feature or device to provide the desired variable force at the rotor and stator interface. In another example, the linear actuator includes one or more air pistons or pneumatic devices used to generate the variable force between the rotor and stator in response to an electrical control signal. In yet another example, one or more hydraulic actuators are used to generate the variable force under the control of a hydraulic control system. The control signals applied to the hydraulic control system are independent of the flow control of the liquid chromatography system although the hydraulic control signals and flow control signals may be synchronized or otherwise related in time. Electrical control signals for these embodiments may be provided by an electronic pressure controller to achieve operation of the rotary shear seal valve in a manner consistent to that described above for embodiments based on the piezoelectric actuator.

While the invention has been shown and described with reference to specific embodiments, it should be understood by those skilled in the art that various changes in form and detail may be made therein without departing from the spirit and scope of the invention as recited in the accompanying claims.

What is claimed is:

1. A method for switching a high pressure fluid, the method comprising:
   applying a fixed force between a planar surface of a rotor and a planar surface of a stator, the planar surface of the rotor having a fluidic channel therein and the planar surface of the stator having a first port to receive a fluid and a second port to provide the fluid, the rotor being coupled to a rotor shaft and configured to rotate about a shaft axis; and
   applying a control signal to an electrical or mechanical linear actuator coupled to the rotor to thereby generate a controllable force directed parallel to the shaft axis and between the planar surface of the rotor and the planar surface of the stator, the control signal being responsive to a rotational state of the rotor, a total force between the planar surfaces of the rotor and the stator being substantially equal to a sum of the fixed force and the controllable force.

2. The method of claim 1 wherein the controllable force is applied when the rotor is stationary at one of a first switch position and a second switch position and wherein the controllable force is not applied when the rotor is moving between the first and second switch positions.

3. A rotary shear seal valve, comprising:
   a rotor shaft having a shaft axis;
   an electrical or mechanical linear actuator secured to the rotor shaft and configured to apply a force directed parallel to the shaft axis in response to an applied electrical signal, the force having a magnitude responsive to the applied electrical signal;
   a rotor having a planar surface with a fluidic channel therein, the rotor being coupled to the linear actuator and configured to rotate about the shaft axis;
   a stator having a planar surface disposed parallel to and in contact with the planar surface of the rotor, the planar surface of the stator having a first port to receive a fluid and a second port to provide the fluid; and
   a valve mechanism to apply a substantially fixed force between the planar surfaces of the stator and the rotor, wherein a total force between the planar surfaces of the rotor and the stator is substantially equal to a sum of the fixed force and the force applied by the linear actuator,
   wherein the fluidic channel conducts the fluid received at the first port to the second port when the rotor is in a first switch position and wherein the fluid is prevented from flowing from the first port to the second port when the rotor is in a second switch position.

4. The rotary shear seal valve of claim 1 wherein the valve mechanism comprises a spring mechanism.

5. The rotary shear seal valve of claim 4 wherein the spring mechanism comprises at least one spring washer.

6. The rotary shear seal valve of claim 1 wherein the first and second ports are configured to couple to a mobile phase path of a liquid chromatography system.

7. The rotary shear seal valve of claim 1 wherein the applied electrical signal is a voltage modulated signal.

8. The rotary shear seal valve of claim 1 wherein the linear actuator comprises a piezoelectric actuator.

9. The rotary shear seal valve of claim 8 wherein the piezoelectric actuator comprises a stack of piezoelectric elements.

10. The rotary shear seal valve of claim 9 wherein the piezoelectric elements are ring-shaped piezoelectric elements.

11. The rotary shear seal valve of claim 1 wherein the electrical or mechanical linear actuator comprises a stepper motor.

12. The rotary shear seal valve of claim 1 wherein the electrical or mechanical linear actuator comprises a magnetic actuator.

* * * * *

UNITED STATES PATENT AND TRADEMARK OFFICE
CERTIFICATE OF CORRECTION

PATENT NO.         : 9,169,934 B2
APPLICATION NO.    : 14/114330
DATED              : October 27, 2015
INVENTOR(S)        : Bernard Bunner, Joseph Michienzi and Keith Fadgen Page 1 of 1

It is certified that error appears in the above-identified patent and that said Letters Patent is hereby corrected as shown below:

In the Claims

Column 8, Line 61, Claim 4:
• Replace the number "1" after claim with "3"

Column 8, Line 65, Claim 6:
• Replace the number "1" after claim with "3"

Column 9, Line 1, Claim 7:
• Replace the number "1" after claim with "3"

Column 9, Line 3, Claim 8:
• Replace the number "1" after claim with "3"

Column 9, Line 10, Claim 11:
• Replace the number "1" after claim with "3"

Column 9, Line 13, Claim 12:
• Replace the number "1" after claim with "3"

Signed and Sealed this
Fifteenth Day of March, 2016

Michelle K. Lee
*Director of the United States Patent and Trademark Office*